United States Patent
Shelley, Jr. et al.

(10) Patent No.: US 9,791,365 B2
(45) Date of Patent: Oct. 17, 2017

(54) SYSTEM AND METHOD FOR MEASURING THERMAL DEGRADATION OF COMPOSITES

(71) Applicant: The Boeing Company, Chicago, IL (US)

(72) Inventors: Paul H. Shelley, Jr., Lakewood, WA (US); Gregory J. Werner, Lacey, WA (US); Milan Milosevic, Westport, CT (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/855,892

(22) Filed: Sep. 16, 2015

(65) Prior Publication Data
US 2017/0074782 A1    Mar. 16, 2017

(51) Int. Cl.
*G01N 21/27* (2006.01)
*G01N 21/33* (2006.01)
*G01N 21/64* (2006.01)

(52) U.S. Cl.
CPC ............. *G01N 21/27* (2013.01); *G01N 21/33* (2013.01); *G01N 21/6456* (2013.01)

(58) Field of Classification Search
CPC ..... G01N 21/27; G01N 21/33; G01N 21/6456
See application file for complete search history.

(56) References Cited

U.S. PATENT DOCUMENTS

| | | | |
|---|---|---|---|
| 3,244,073 A | 4/1966 | Bouwers et al. | |
| 6,903,339 B2 * | 6/2005 | Shelley | G01B 11/0625 250/339.01 |
| 2005/0067569 A1 * | 3/2005 | Shelley | G01N 21/55 250/341.8 |
| 2014/0273240 A1 * | 9/2014 | Georgeson | G01N 31/229 436/7 |

FOREIGN PATENT DOCUMENTS

| | | |
|---|---|---|
| EP | 0 267 766 | 5/1988 |
| EP | 2 778 661 | 9/2014 |
| WO | 2014/032744 | 3/2014 |

OTHER PUBLICATIONS

EP, Extended European Search Report and Opinion; European Patent Application No. 16186421.0, 10 pages (Jan. 25, 2017).
Fisher, W. G. et al., "Nondestructive Inspection of Graphite-Epoxy Composites for Heat Damage Using Laser-Induced Fluorescence"; Applied Spectroscopy; The Society for Applied Spectroscopy; vol. 49, No. 9, XP000524517; pp. 1225-1231 (Sep. 1, 1995).

* cited by examiner

Primary Examiner — Casey Bryant
(74) Attorney, Agent, or Firm — Thompson Hine LLP

(57) ABSTRACT

A system for measuring thermal degradation of composites, may include a housing having an interior with an opening shaped to expose a test area of the composite to be tested to the interior; a light-emitting diode that emits primarily ultraviolet radiation, the diode mounted on the housing to direct the ultraviolet radiation into the interior and through the opening; an image sensor mounted on the housing and (Continued)

open to the interior to receive radiation emitted from the test area passing through the opening into the interior; and an image processor connected to receive a signal from the image sensor, the image processor determining a presence or absence of thermal degradation of the test area in response to the signal.

20 Claims, 2 Drawing Sheets

SYSTEM AND METHOD FOR MEASURING THERMAL DEGRADATION OF COMPOSITES

TECHNICAL FIELD

This disclosure relates to systems and methods for non-destructive testing of materials and, more particularly, to systems and methods for detecting and measuring thermal degradation of composite materials.

BACKGROUND

The structural components of vehicles, such as aircraft, are comprised of increasing amounts of composite materials, such as carbon fiber reinforced plastic (CFRP). Heat damage to such composite materials may occur from a number of causes, including a lightning strike, an electrical short in wiring, or an overheated component. When heated to an elevated temperature for an extended period of time, composite materials may lose some of their desirable mechanical properties. In particular, such heating may reduce the ability of the composite materials to withstand mechanical stresses.

Currently, non-destructive testing of composite material is performed with a portable FTIR (Fourier Transform Infrared) spectrometer to identify any potential degradation. Such portable devices are relatively large, and expensive. An FTIR spectrometer uses the selective IR (infrared) absorbance of different chemical compounds, so that oxidized carbon is easily distinguished from unoxidized material. The relatively grainy consistency of the composite material leads to results that may be highly variable on a scale of the inspection area, which typically is 1 mm in diameter. This requires measurements to be made on a statistically significant number of different nearby spots in order to reach a reliable conclusion on the degree of damage.

Such FTIR spectrometers are relatively large and expensive. Further, their size does not lend their use to inspection of composite materials in difficult-to-reach areas. Accordingly, there is a need for a small, portable system for measuring thermal degradation of composites.

SUMMARY

This disclosure is directed to a system and method for measuring thermal degradation of composites that utilizes a small, hand-held detection device that is relatively inexpensive to manufacture and operate. In one aspect, a system for measuring thermal degradation of composites may include a housing having an interior with an opening shaped to expose a test area of the composite to be tested to the interior; a light-emitting diode that emits primarily ultraviolet radiation, the diode mounted on the housing to direct ultraviolet radiation into the interior and through the opening; an image sensor mounted on the housing and open to the interior to receive radiation emitted from the test area passing through the opening into the interior; and an image processor connected to receive a signal from the image sensor, the image processor determining a presence or an absence of thermal degradation of the test area in response to the signal.

In another aspect, a system for measuring thermal degradation of composites may include a housing having a side wall, a top wall and a bottom wall forming an interior, the housing having an opening shaped to expose a sample to be tested to the interior; a light-emitting diode that emits primarily ultraviolet radiation, the diode mounted in the side wall of the housing to direct ultraviolet radiation into the interior and through the opening, and including a high-pass filter that allows only ultraviolet radiation from the light-emitting diode to enter the interior; an ellipsoid mirror mounted on the side wall within the interior and shaped and positioned to receive the ultraviolet radiation and reflect the ultraviolet radiation through the opening; an image sensor mounted on the top wall of the housing and open to the interior to receive radiation emitted from the sample passing through the opening, a first parabolic mirror mounted on the top wall within the interior, and a second parabolic mirror mounted on the bottom wall within the interior, the first parabolic mirror facing the second parabolic mirror such that radiation emitted by the sample is reflected from the first mirror to the second mirror, and from the second mirror to the image sensor; and an image sensor connected to receive a signal from the image sensor, the image processor having a display that indicates a presence or an absence of thermal degradation of the sample in response to the signal.

In yet another aspect, a method for measuring thermal degradation of composites may include actuating a light-emitting diode to emit primarily ultraviolet radiation into an interior of a housing; directing the ultraviolet radiation from the interior of the housing through an opening in the housing to a portion of a sample to make the sample fluoresce visible light radiation; detecting the visible light radiation by an image sensor mounted on the housing and open to the interior; receiving a signal from the image sensor by an image processor indicative of a property of visible light radiation detected by the image sensor; and providing a display in response to the signal received by the image processor indicative of a presence or an absence of thermal degradation of the portion of the sample.

Other objects and advantages of the disclosed system and method for measuring thermal degradation of composites will be apparent from the following description, the accompanying drawings, and the appended claims.

DETAILED DESCRIPTION

Figure 1:
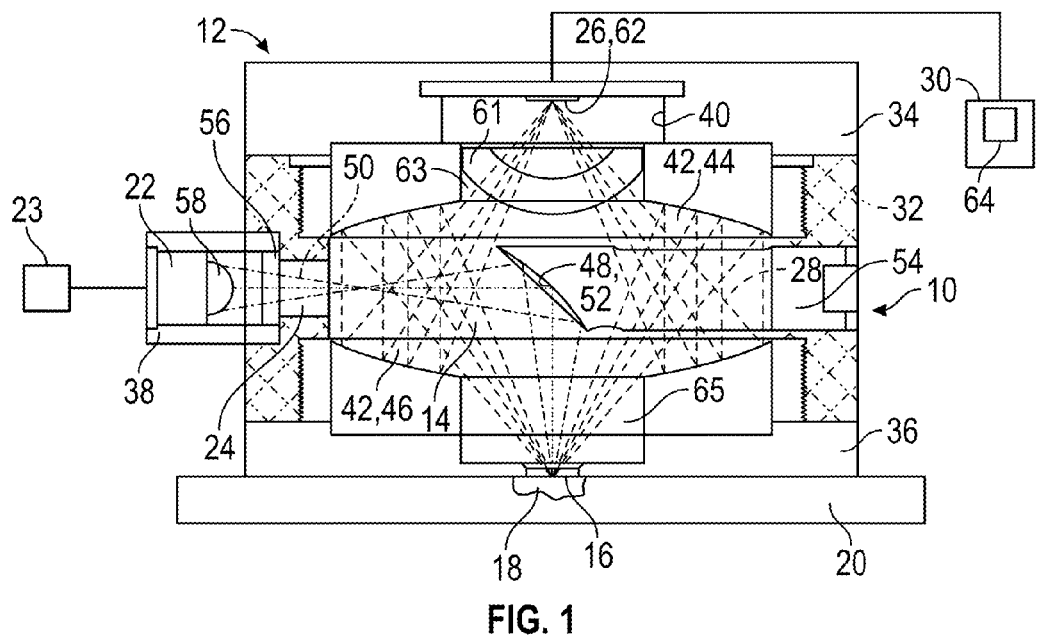
FIG. 1 is a schematic side elevation of an aspect of the system for measuring thermal degradation of composites.

As shown in FIG. 1, a system for measuring thermal degradation of composites, generally designated 10, may include a housing 12 forming an interior 14 with an opening 16 shaped to expose a test area 18 of a composite 20 to be tested. A light-emitting diode (LED) 22 may be powered by a power supply 23 and emits ultraviolet radiation, or emits primarily ultraviolet radiation. The light-emitting diode 22 may be mounted on the housing 12 and oriented to direct ultraviolet radiation into the interior 14 through a side opening 24 to direct the ultraviolet radiation to the opening 16. An image sensor 26 is mounted on the housing 12 and open to the interior 14 to receive radiation 28 emitted from the test area 18 passing through the opening 16 into the interior 14. An image processor 30 may be connected to receive a signal from the image sensor 26. As will be described in detail below, the image processor may determine a presence or absence of thermal degradation of the test area 18 in response to the signal from the image sensor 26.

In an embodiment, the housing 12 may include a side wall 32, an upper wall 34 attached to the side wall, and a lower wall 36 attached to the side wall. The side wall 32 may be generally cylindrical in shape, and the upper wall 34 and lower wall 36 may be disk shaped, matching the side wall in diameter. The side wall may include the side opening 24 that receives the diode 22. The side wall 32, the upper wall 34, and the lower wall 36 may combine to define the interior 14 of the housing 12. The light-emitting diode 22 may be mounted within a housing 38 that is attached or mounted on the side wall 32. The image sensor 26 may be mounted in a recess 40 formed in the upper wall 34. The opening 16 may be formed in the lower wall 36.

In an embodiment, the housing 12 may include a first reflective surface 42 positioned in the interior 14. The first reflective surface 42 may be shaped and positioned to receive the radiation 28 emitted from the test area 18, and reflect the radiation emitted or fluoresced from the test area to the image sensor 26. Also in the embodiment, the first reflective surface 42 may include a first parabolic mirror 44 mounted on the upper wall 34, and a second parabolic mirror 46 mounted on the lower wall 36. The first and second parabolic mirrors 44, 46 may be shaped and positioned such that the first parabolic mirror receives the radiation 28 emitted or fluoresced from the test area 18 and reflects the radiation emitted from the test area to the second parabolic mirror 46. The second parabolic mirror may be shaped and positioned to reflect the radiation 28 emitted from the test area 18 and reflected from the first parabolic mirror 44 to the image sensor 26. In an embodiment, the first and second parabolic mirrors 44, 46 may face each other, and in still other embodiments, may lie on a common central axis and be parallel to each other.

The system 10 may include a second reflective surface 48 mounted in the interior 14 of the housing 12 and positioned to receive the ultraviolet radiation 50 from the light-emitting diode 22. The second reflective surface 48 may be positioned to reflect the ultraviolet radiation 50 the opening 16 in the housing 12, where it impinges on the test area 18 of the composite 20 to be tested. In an embodiment, the second reflective surface 48 may include an ellipsoid mirror 52. The ellipsoid mirror 52 may be attached to or mounted on a holder 54 that, in turn, may be attached to the side wall 32 of the housing 12. Also in an embodiment, the second reflective surface 48, ellipsoid mirror 52 and holder 54 may be positioned between the first and second parabolic mirrors 44, 46, respectively, within the interior 14 of the housing 12.

The system 10 also may include a high-pass filter 56 that may be mounted in the housing 12, and in particular in the opening 24 in the side wall 32. The high-pass filter 56 may be selected to permit only the ultraviolet component of the primarily ultraviolet radiation 50 from the LED 22 to pass through the high-pass filter and enter the interior 14 of the housing 12. The LED 22 may include an integral ball lens 58 shaped and positioned to focus the primarily ultraviolet radiation 50 emitted by the LED 22. The primarily ultraviolet radiation 50 may be focused by the ball lens 58 into the first focal point of the ellipsoid mirror 52, where it may be reflected through the opening 16 in the bottom wall 36 into the second focal point of the ellipsoid mirror, into which the test area 18 of the composite 20 to be tested is placed.

The system 10 may include an ultraviolet-blocking filter 61 that is selected to allow visible light radiation 28 to pass, but block ultraviolet radiation. The ultraviolet-blocking filter 61 may be mounted on the housing 12 such that only visible light radiation 28 reaches the image sensor 26 from the interior 14 of the housing. In an embodiment, the first parabolic mirror 44 may include a circular recess 63, and the ultraviolet-blocking filter 61 may be shaped to fit within the recess immediately adjacent the image sensor 26. In an embodiment, the image sensor 26 may be a digital camera 62. Similarly, in an embodiment, the second parabolic mirror 46 may include a circular passage 65 that connects the opening 16 with the interior 14 of the housing 12.

Also in an embodiment, the image processor 30 may be selected from, or operated by software loaded in, a laptop computer and a mobile device, such as a handheld tablet computer. In embodiments, the laptop computer or mobile device also may contain the power supply 23 for the LED (FIG. 1). The connection between the image sensor 26 and the image processor 30 may be hard wired or wireless. The image processor 30 may be programmed to compare a ratio of color intensities of the radiation 28 emitted from the test area 18 of two colors selected from red and green, red and blue, and blue and green. The image processor 30 may include a display 64 that indicates the presence or the absence of thermal degradation of the test area 18, dependent upon the comparison of the ratios to the stored values.

The system 10 may operate by energizing the ultraviolet LED 22, which emits ultraviolet radiation 50 through high-pass filter 56 into the interior 14 of the housing 12. The ultraviolet radiation 50 is reflected by the ellipsoid mirror 52 downwardly through the circular passage 65 and opening 16, where it contacts the test area 18 of the composite material 20. This irradiation may cause the composite material 20 in the test area 18 to fluoresce in the visible light range, emitting radiation 28 in the visible light range that is reflected by the first parabolic reflector 44 to the second parabolic reflector 46, and from the second parabolic reflector 46 upwardly through the ultraviolet-blocking filter 61 to the image sensor 26. The pixels of the image sensor 26, which may be a digital camera 62, receive the visible light radiation 28 fluoresced from the test area 18.

Figure 3A:
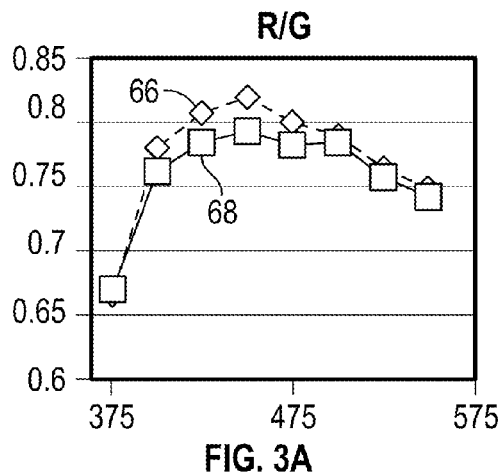
FIGS. 3A, 3B, and 3C are graphs of the ratio of intensity of fluoresced radiation versus exposed temperature of a first side of actual test specimens of composite material in which data points are ratios of intensities of the red to green, red to blue, and blue to green segments of the visible light spectrum, using two methods of calculating ratios.
Figure 3B:
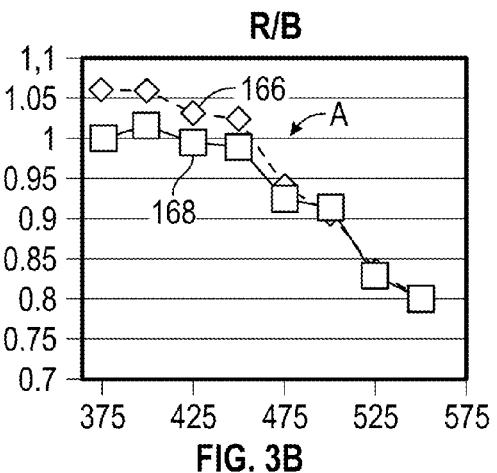
Figure 3C:
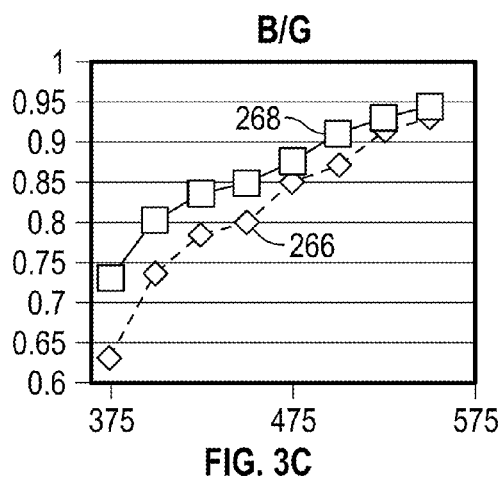
Figure 4A:
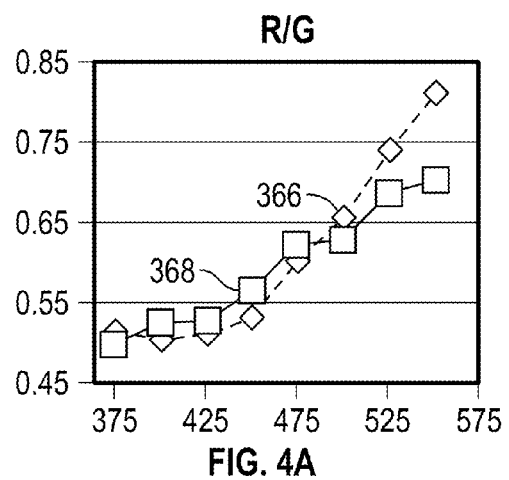
FIGS. 4A, 4B, and 4C are graphs of the ratio of intensity of fluoresced radiation versus exposed temperature of a second, opposite side of the actual test specimens of composite material in which data points are ratios of intensities of the red to green, red to blue, and blue to green segments of the visible light spectrum, using two methods of calculating ratios.
Figure 4B:
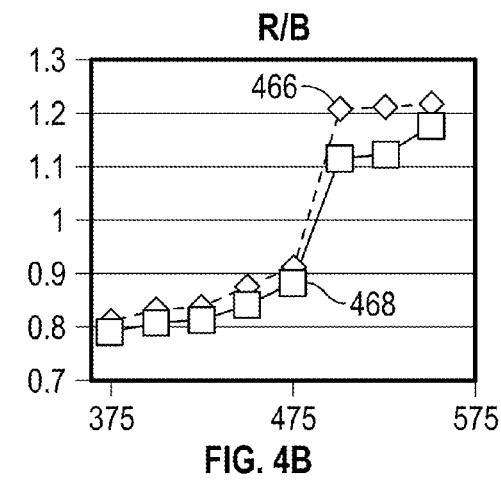
Figure 4C:
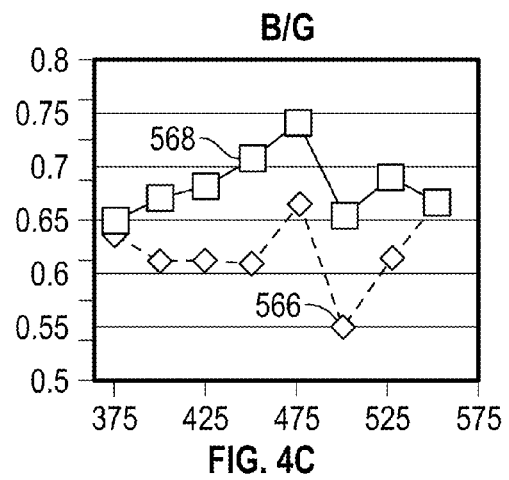

FIGS. 3A, 3B, and 3C, and 4A, 4B, and 4C show the results of tests of the disclosed system 10, measuring the intensity of the radiation 28 received by the image sensor 26, which in the test was a digital camera 62, for different colors of the visible light radiation 28 for 8 different specimens of composite carbon fiber reinforced plastic material, each of which would represent test area 18 (FIG. 1). FIGS. 3A-3C are the results taken of a first side taken at 4 random points on each of the 8 specimens, and FIGS. 4A-4C are the results taken of the second or opposite side of the same 8 specimens taken at 4 random points each. Each of the 8 specimens was heated to a different temperature for the same one-hour time interval. The temperatures at which the 8 specimens were heated ranged from 375° F. to 550° F. in 25° F increments.

The intensity of color fluorescing from a test specimen of composite material using the disclosed system 10 may vary with the temperature and the duration of thermal exposure of the test specimen. FIGS. 3A-3C and 4A-4C each show an image file created by the image processor 30 from a signal received by the image sensor 26 that may be converted by software in the image processor into three matrices: red, green, and blue, where each matrix element may display the intensity of a particular pixel for red, green, and blue color. In order to avoid alignment and excitation light variability, the ratios of red/green, red/blue, and blue/green were calculated, thus making the ratios insensitive to alignment, intensity of the light-emitting diode 22, gain, or exposure times used by the camera 62. On the x or horizontal axis of each graph, the temperature of a side of the test specimen of composite material, representing test area 18, is plotted. On the y or vertical axis, the ratio of intensities of the colors is indicated for that temperature. The camera 62 may read some intensity even when the LED 22 is turned off. In such case, that intensity is measured and subtracted from the readings made when the LED is turned on.

In FIG. 3A, the small, diamond-shaped data points 66 connected by the broken line represent the ratio of red visible light intensity to green visible light intensity from the 8 test specimens after exposures to 375° F., 400° F., 425° F., 450° F., 475° F., 500° F., 525° F., and 550° F. for one hour. The data points represented by the small, diamond-shaped data points 66 are calculated using a first method, by ratioing the intensities pixel-by-pixel, and then calculating the average ratio over the entire digital camera image. The data points represented by the larger squares 68 in FIG. 3A connected by a solid line represent the ratio of red visible light intensity to green visible light intensity for the same temperatures and time interval of the 8 specimens, using a second method in which the ratio was calculated by first taking the average of the color intensity over all the pixels of the digital camera 62 for red visible light and for green visible light, and then calculating the ratio of the two average values.

In FIG. 3B, data points are plotted for the same temperature values for ratios of red visible light intensity versus blue visible light intensity. Small, diamond-shaped data points 166 represent the ratio of red to blue intensity using the first method of ratioing the intensities pixel-by-pixel, then calculating the average ratio over the entire digital camera image, and the large squares 168 represent the ration of red to blue intensity using the second method of taking the average of the color intensity over all the pixels for red to blue, then calculating the ration of the two average values, for each of the 8 specimens heated to the temperatures ranging from 375° F. to 550° F. in 25° F. increments. Similarly, FIG. 3C shows data points plotted for blue to green intensity for the 8 samples using the first ratioing method, represented by small diamonds 266, and using the second ratioing method, represented by large squares 268. FIG. 4A shows data points plotted for red to green intensity for the second or opposite sides of the 8 samples using the first ratioing method, represented by small diamonds 366, and large squares 368, using the second ratioing method. FIG. 4B shows data points plotted for red to blue intensity for the second or opposite sides of the 8 samples using the first ratioing method, represented by small diamonds 466, and large squares 468, using the second ratioing method; and FIG. 4C shows data points plotted for blue to green intensity for the second or opposite sides of the 8 samples using the first ratioing method, represented by small diamonds 566, and large squares 568, using the second ratioing method.

Useful data may be obtained from those of the graphs that show a continuous increase or decrease with temperature. Accordingly, the graphs of FIGS. 3B and 4B may be the most useful for determining whether the particular composite material 20 being measured has been damaged or degraded by heating. With respect to FIG. 3B, there is a noticeable decrease in intensity at a temperature at approximately 450° F. on the x axis at A. Similarly, in FIG. 4B, there is a noticeable increase in intensity that begins at about 450° F. on the x axis. That temperature and time interval may be considered significant for effecting thermal degradation of a composite material. Accordingly, such ratio values may be stored in the image processor 30, and compared with a test made of the test area 18. By measuring the intensities and calculating the aforementioned ratios, the exposure temperature may be back calculated by the image processor 30 (FIG. 1). Other types of composite materials, which may degrade at different time-temperature combinations, and be indicated by different ratios, may be stored in image processor 30 as well.

Figure 2:
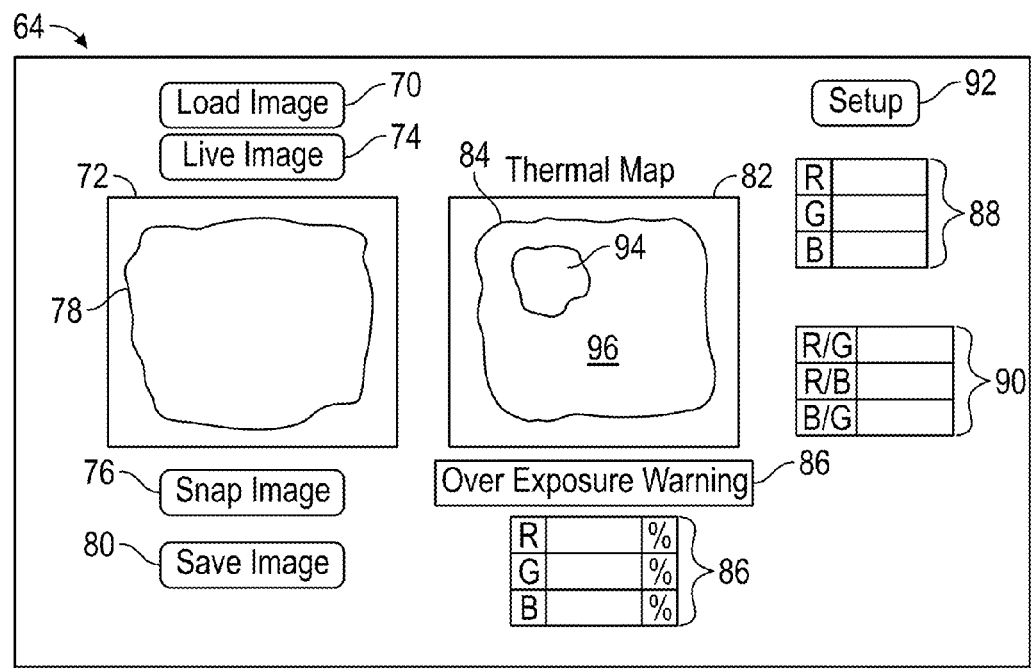
FIG. 2 is a schematic representation of a display of data received by the system of FIG. 1.

As shown in FIG. 2, a display 64 may include the screen illustrated in the figure, either as hardware or as a virtual screen on a computer display screen, and appropriate software to operate it. The display 64 may include a touch screen or virtual button 70, marked "LOAD IMAGE" for loading a previously saved image into the left frame 72. The virtual or actual button 74 marked "LIVE IMAGE" may switch the left frame 72 to the live image from the image sensor 26 mounted in the housing 12. The actual or virtual button 76 marked "SNAP IMAGE" actuates the image sensor 26 to take a snapshot from a live image of the test area 18 and place it into the left frame 72. In FIG. 2, the image 78 shown in the left frame may be such a live image. The actual or virtual button 80 marked "SAVE IMAGE" may be actuated to save the snapped image 78 to a disc or other non-volatile storage or memory.

The right frame 82 of the display 64 may display the processed image 84, which may take the form of a thermal map of the snapped or loaded, but not of the live, image. The display 64 also may include an analog-to-digital saturation or overexposure warning 86 that may indicate the percent of the over exposed pixels for red, green, and blue, separately. The red, blue, and green text boxes 88 may display an average value of red, green, and blue color in the snapped and loaded image, and boxes 90 may display the ratios of red to green, red to blue, and blue to green and display the corresponding ratios. The virtual or actual button 92 marked "SETUP" may open a setup window with access to camera settings for the image sensor 26, save to folder selection and other features of the display 64. The thermal map 82 may use the developed model to assign and color code the temperature of each pixel.

Accordingly, in embodiments, the display 64 may indicate thermal degradation by appropriate color coding of the image 84 on the thermal map 82 if the ratio of either red/green, red/blue, or blue/green is selected from less than a stored value, or greater than a stored value. In an embodiment, the display 64 may activate a first indicator, such as a color 94 area, if the image processor 26 detects thermal degradation of the test area 18, and the display 64 may activate a second indicator 96 if the image processor does not detect thermal degradation in a portion of the test area. In embodiments, the image processor 26 may assign a first color 96 to an area of no thermal degradation, and a second color 94 to an area of thermal degradation in the test area 18. As shown in FIG. 2, the display 64 may display in window 82 a composite image of the test area 18 in which areas of no thermal degradation 96 are colored with a first color, and areas of thermal degradation 94 are colored with a second color.

A method embodied in the system 10 for measuring thermal degradation of composites may include actuating the light-emitting diode 22 to emit primarily ultraviolet radiation 50 into an interior 14 of the housing 12. The ultraviolet radiation 50 may be directed by the ellipsoid mirror 52 from the interior 14 of the housing 12 through the opening 16 in the housing to a test area 18 of the material composite 20 to be tested. This ultraviolet radiation may cause the composite material 20 to fluoresce visible light radiation 28. The visible light radiation 28 may be reflected first from the first parabolic mirror 44 to the second parabolic mirror 46, and from the second parabolic mirror through the ultraviolet filter 61 to the image sensor 26. The image sensor 26 detects the visible light radiation and generates a signal corresponding to the intensity of the radiation in the colors red, blue, and green. This signal may be processed by the image processor 30 to a display 64 that indicates a presence or absence of thermal degradation of the test area 18 of the composite 20.

The system 10 and method for measuring thermal degradation of composites described herein may be provided in a housing 12 that is small and handheld. The image processor 30 likewise may be compact and portable, and may be in the form of a laptop, handheld device, or tablet. The display 64 may provide a rapid and easily discernible indication of the presence of thermal degradation of a composite material 20.

While the systems and methods for measuring thermal degradation of composites described herein constitute preferred embodiments of the method and system, the scope of the disclosure is not limited to these precise methods and systems, and changes may be made therein without departing from the scope of the appended claims.

What is claimed is:

1. A system for measuring thermal degradation of composites, the system comprising:
   a housing having an interior with an opening shaped to expose a test area of the composite to be tested to the interior;
   a light-emitting diode that emits primarily ultraviolet radiation, the diode mounted on the housing to direct the ultraviolet radiation into the interior and through the opening;
   an image sensor mounted on the housing and open to the interior to receive radiation emitted from the test area, in response to the ultraviolet radiation, passing through the opening into the interior and generate a signal in response thereto;
   the housing having a first reflective surface positioned in the interior that is shaped and positioned to receive the radiation emitted from the test area and reflect the radiation emitted from the test area to the image sensor, the first reflective surface including a first parabolic mirror mounted on the upper wall and a second parabolic mirror mounted on the lower wall, the first and the second parabolic mirrors shaped and positioned such that the first parabolic mirror receives the radiation emitted from the test area and reflects the radiation emitted from the test area to the second parabolic mirror, and the second parabolic mirror is shaped and positioned to reflect the radiation reflected from the first parabolic mirror to the image sensor;
   a second reflective surface mounted in the interior and positioned between the first and the second parabolic mirrors to receive the ultraviolet radiation from the light-emitting diode and reflect the ultraviolet radiation to the opening in the housing; and
   an image processor connected to receive the signal from the image sensor, the image processor programmed to determine a presence or an absence of thermal degradation of the test area in response to the signal, and the image processor including a display that displays one or both of a live image of the test area and a thermal map of the test area.

2. The system of claim 1, wherein the housing includes a side wall, an upper wall attached to the side wall, and a lower wall attached to the side wall, the side wall, the upper wall and the lower wall defining the interior of the housing.

3. The system of claim 2, wherein the light-emitting diode is mounted in the side wall; the image sensor is mounted in the upper wall; and the opening is formed in the lower wall.

4. The system of claim 3, wherein the second parabolic mirror includes a circular passage that connects the opening with the interior of the housing.

5. The system of claim 4, wherein the first parabolic mirror includes a recess that receives an ultraviolet-blocking filter adjacent the image sensor.

6. The system of claim 1, wherein the housing includes a generally cylindrical side wall, a disk-shaped upper wall and a disk-shaped lower wall that combine to define the interior; and wherein the side wall includes a side opening that receives the light-emitting diode.

7. The system of claim 1, wherein the second reflective surface includes an ellipsoid mirror.

8. The system of claim 7, wherein the ellipsoid mirror is attached to a holder that is attached to the side wall.

9. The system of claim 1, further comprising a high-pass filter mounted in the housing, the high-pass filter permitting only the ultraviolet component of the primarily ultraviolet radiation from the light-emitting diode to pass through the high-pass filter and enter the interior.

10. The system of claim 9, wherein the light-emitting diode includes a ball lens to focus the primarily ultraviolet radiation emitted by the light-emitting diode.

11. The system of claim 1, further comprising an ultraviolet filter that allows visible light radiation to pass, the ultraviolet filter mounted on the housing such that only visible light radiation reaches the image sensor from the interior.

12. The system of claim 1, wherein the image sensor is a digital camera.

13. The system of claim 1, wherein the image processor is selected from a laptop computer and a mobile device.

14. The system of claim 1, wherein the image processor is programmed to compare a ratio of color intensities of the radiation emitted from the test area of two colors selected from red and green, red and blue, and blue and green; compare the ratio to a stored value; and the image processor is further programmed to indicate the presence or the absence of thermal degradation in the test area dependent upon the comparison of the ratio to the stored value on the display.

15. The system of claim 14, wherein the image processor is programmed to indicate thermal degradation on the display if the ratio is selected from less than the stored value, and greater than the stored value.

16. The system of claim 15, wherein the image processor is programmed to activate a first indicator on the display if the image processor detects thermal degradation of the test area, and a second activator on the display if the image processor does not detect thermal degradation of the test area.

17. The system of claim 15, wherein the image processor is programmed to assign a first color to an area of no thermal degradation, and a second color to an area of thermal degradation, on the thermal map of the display.

18. The system of claim 17, wherein the image processor is programmed to actuate the display to show a composite image of the test area in which areas of no thermal degradation are colored with the first color, and areas of thermal degradation are colored with the second color.

19. A system for measuring thermal degradation of composites, the system comprising:
   a housing having an interior with a side wall, a top wall, and a bottom wall forming an interior, the housing having an opening shaped to expose a test area to be tested to the interior;
   a light-emitting diode that emits primarily ultraviolet radiation, the diode mounted in the side wall of the housing to direct the ultraviolet radiation into the interior and through the opening, and including a high-pass filter that allows only ultraviolet radiation from the light-emitting diode to enter the interior;
   an ellipsoid mirror mounted on the side wall within the interior and shaped and positioned to receive the ultraviolet radiation and reflect the ultraviolet radiation through the opening;
   an image sensor mounted on the top wall of the housing and open to the interior to receive radiation emitted from the test area passing through the opening and generate a signal in response thereto;
   a first parabolic mirror mounted on the top wall within the interior, and a second parabolic mirror mounted on the bottom wall within the interior, the first parabolic mirror facing the second parabolic mirror such that the radiation emitted by the test area is reflected from the first parabolic mirror to the second parabolic mirror, and from the second parabolic mirror to the image sensor, and wherein the ellipsoid mirror is positioned between the first parabolic mirror and the second parabolic mirror; and
   an image processor connected to receive a signal from the image sensor, the image processor having a display, the image processor programmed to determine a presence or an absence of thermal degradation of the test area in response to the signal, and the image processor is programmed to actuate the display to display one or both of a live image of the test area and a thermal map of the test area.

20. A method for measuring thermal degradation of composites, the method comprising:
   actuating a light-emitting diode to emit primarily ultraviolet radiation into an interior of a housing;
   reflecting the ultraviolet radiation from the light-emitting diode by a second reflective surface mounted in the interior and positioned between a first parabolic mirror and a second parabolic mirror positioned in the interior of the housing through an opening in the housing to a portion of a test area to make the test area fluoresce visible light radiation;
   reflecting the visible light radiation by the first parabolic mirror that receives the visible light radiation emitted from the test area to the second parabolic mirror;
   reflecting the visible light radiation from the first parabolic mirror by the second parabolic mirror to the image sensor;
   detecting the visible light radiation reflected by the second parabolic mirror by an image sensor mounted on the housing and open to the interior, and generating a signal by the image sensor in response thereto;
   receiving the signal from the image sensor by an image processor indicative of a property of visible light radiation detected by the image sensor; and
   actuating a display by the image processor in response to the signal received by the image processor indicative of a presence or an absence of thermal degradation of the portion of the test area.

* * * * *